United States Patent [19]

Smith

[11] Patent Number: 5,464,775
[45] Date of Patent: Nov. 7, 1995

[54] METHOD OF DETECTING ADULTERANT IN URINE

[75] Inventor: Jack V. Smith, St. Petersburg, Fla.

[73] Assignee: Chimera Research and Chemical, Inc., Seminole, Fla.

[21] Appl. No.: 281,296

[22] Filed: Jul. 27, 1994

Related U.S. Application Data

[63] Continuation-in-part of Ser. No. 760,879, Sep. 16, 1991, abandoned.

[51] Int. Cl.$^6$ ................................................ G01N 33/48
[52] U.S. Cl. .................... 436/63; 436/128; 436/169; 436/901
[58] Field of Search ............................ 436/63, 128, 164, 436/901

[56] References Cited

U.S. PATENT DOCUMENTS

| | | | |
|---|---|---|---|
| 3,932,131 | 1/1976 | Rolfo-Fontana et al. | 436/12 |
| 4,605,615 | 8/1986 | Ishikawa et al. | 435/25 |
| 4,845,028 | 6/1989 | Imamura et al. | 435/15 |
| 4,992,381 | 2/1991 | Crain et al. | 436/164 |
| 5,069,878 | 12/1991 | Ehrenkranz | 422/61 |

OTHER PUBLICATIONS

Mikkeisen et al. "Adulterants Causing False Negatives in Illicit Drug Testing", Clin. Chem. 34/11 2333–2336 (1988).
T. Vu Due "EMT Test for Drugs of Abuse: Interference by Liquid Soap Preparation" Clin. Chem. vol. 31, No. 4 pp. 658–659 (1985).
Anderson et al. "Specific Conductivity of Urine and Sensitivity of Enzyme Immunoassay Methods of Analysis for Drugs of Abuse" Clin. Chem 23/4 pp. 751–753 (1977).
Van der Siooten et al. "Comparison of the EMIT Opiato Assay and GC–MS Determination of Morphine and Codine in Urine" Clin. Chem. 22/7, pp. 1110–1111 (1976).
Duarte "Renal Function Test", pub. Little, Brown and Co. Boston, pp. 13 and 25 (No Publication Date).
Allen et al. "Specificity of the EMIT Drug Abuse Urine Assay Methods" Copyright© 1981 by Marcel Pekker, Inc. pp. 1043–1065.
Kim "Interference by Nacl with the EMIT Method of Analysis for Drugs of Abuse" Clin. Chem. 22/11 pp. 1935–1936 (1976).
"Urinalysis Collection Handbook For Federal Drug Testing Programs" Sep. 1988, U.S. Dept. of Health and Human Services p. 2.
"Medical Review Officer Manual: A Guide to Evaluate Urine Drug Analysis", Sep. 1988, U. S. Dept. of Health and Human Services, pp. 29–30.
BIOSIS 89: 93148 "Adulterants Causing False/Negatives in Illicit Drug Testing" Mikkelsen et al.

*Primary Examiner*—Lyle A. Alexander
*Attorney, Agent, or Firm*—Herbert W. Larson

[57] ABSTRACT

A method of detecting gluteraldehyde adulterant in a urine sample. An aliquot of urine is inserted into an automatic chemical analyzer and a spectrophotometric absorbance reading is taken. Thereafter, the aliquot is mixed with a reagent mixture containing a carbonyl indicator and a second spectrophotometric absorbance reading is taken and compared to the first reading.

8 Claims, No Drawings

METHOD OF DETECTING ADULTERANT IN URINE

PRIOR APPLICATION

This application is a continuation-in-part of application Ser. No. 07/760,879 filed Sep. 16, 1991, now abandoned.

BACKGROUND OF THE INVENTION

This invention relates to a single reagent system for use in determining the presence of commercially available adulterants in urine, or other fluids, being screened for drugs of abuse. This invention is particularly useful in automated analyzers used in screening for drugs of abuse.

As the use of illicit drugs in the workplace, public transportation, professional and amateur athletics and the like has grown, public concern for the health and safety of individuals, as well as concern for the negative impact of such drug use on productivity of industry, and its inherent economic impact, and the general well being and health of the community at large has grown as well. Such concern has led to the use of analysis of urine as a way to detect and deter drug use. Such testing for drugs of abuse in industry, as for prospective and current employees, military personnel, transportation, employees, professional and amateur athletes, as well as people under supervision of the criminal justice system, has become a relative common occurrence.

Because of the intrusive nature of such testing commonly performed by examining a urine sample, the testing procedure must withstand vigorous scrutiny. Since a positive test result of screening for drugs of abuse may have serious impact on the life of a person being tested, the incentive for the drug user to alter the test specimen is high. The users of drugs of abuse have developed a number of ways to adulterate the collected specimen, thus attempting to produce a false negative result in the drug screening test being conducted.

A user of drugs of abuse may attempt to affect the test results, thus producing a false negative test result, or upon occassion, a false positive result, as by: 1) dilution—efforts to reduce the drug concentration in the urine sample; b) substitution— substitution for liquids such as clean (that is, drug-free) urine, sosa, tea, apple juice for the drug-containing sample; or c) adulteration—addition to the urine specimen of foreign material in an attempt to invalidate the test.

Illicit drug users have learned to falsify urine screening tests by in vitro adulteration of urine sample by the addition of several readily available agents, including household products; i.e., Nacl, soap, such as hand or dish soap, bleach, finger nail polish remover, vinegar, Drano, $NaNCO_3$, Visine, fingernail polish, Gold Seal Tea (available in natural food stores), or hydrogen peroxide ($H_2 O_2$), together with commercially available adulteration products, such as "Urine-Aid" (gluteraldehyde).

Additionally, users of drugs of abuse may eliminate some drugs more rapidly from their bodies by altering their urinary pH. Abusers of phencylidine or amphetamines may be treated with $NH_4Cl$ to hasten detoxification, thus increasing the rate at which substances (phencylidine or emphetamines) are eliminated from their bodies. This treatment with $NH_4Cl$ also results in lowering the pH of the user's urine.

While the use of some in vitro adulterants can be eliminated by the direct observation of the test subject during the collection process, such direct observation is often deemed unacceptable. In vivo adulternants represent an additional burden to the screening processor because they are consumed by the drug user several hours or days prior to screening of the sample, and can be detected only by laboratory means.

Such adulteration can affect all three commonly used methods for drugs of abuse, namely: florescent polarization immunoassay (FPIA), radioimmunoassay (RIA), and enzyme immunoassay (EMIT or EIA). Consequently, clinical chemistry literature recommends that testing for drugs of abuse in urine samples include testing for adulterants to identify urine samples which have been adulterated. See Mikkelsen and Ash, "Adulterants Causing False Negatives In Illicit Drug Testing", *Clin. Chem.* 34/11, 2333–2336 (1988); and Warner, "Interference of Common Household Chemicals In Immunoassay Methods For Drugs Of Abuse", *Clin. Chem.*, 35/4, 648–651 (1989).

Accordingly, a need exists for providing an easy and convenient manner by which to make a determination of the presence of adulterants in urine samples which are being tested for drugs of abuse. A further need exists for a convenient manner by which such determinations may be made in conjunction with an automatic analyzing process for drugs of abuse.

SUMMARY OF THE INVENTION

The present invention relates to a method of employing a single channel reagent to detect the presence of a commercially available adulterant i.e., Urine-Aid, gluteraldehyde, in urine or other fluids. This reagent is designed to be used on automated analyzers used for drugs of abuse testing.

The purpose of the reagent used in this process is to facilitate the conducting of testing for adulterants such as gluteraldehyde simultaneously while conducting drug tests on the same automatic analyzer. Specifically, if the presence of an adulterant is detected in the urine, or other sample fluid being tested a false negative reading will result, when tested by a common drug-screening method; namely, EIA (enzyme immunoassay) in testing for drugs of abuse, such as: THC. For example, the adulteration of a urine sample containing THC and its metabolites with a commercial agent such as Urine-Aid, (gluteraldehyde) will result in a false negative for THC by EIA.

The reagent used in this invention permits the technician conducting the test to halt the testing process, or assay, as soon as the presence of the adulterant is detected. The ability to terminate the screening process by ascertaining the presence of an adulterant, would result in reduced technician's efforts and time, providing an economic savings to the testing laboratory. Furthermore, the early interruption and cessation of the automated screening process may facilitate earlier recovery of a substitute specimen from the person being tested, providing more accurate determinations to the agency which had determined the original necessity for the test.

The instant reagent system comprises an aqueous solution of buffers, carbonyl group indicators, and surfactants that effect a color change, depending on the presence of adulterant in the urine, or other sample fluid being tested. The reagent is based on an indicator principle which gives a change (increase) in absorbance in the presence of the urine adulterant. A sample of urine is mixed with the reagent in a specific ratio, and the mixture of urine and reagent will exhibit a change in absorbance, depending on the presence of the adulterant. The change in absorbance may be monitored at a specific wavelength by a UV-visible spectrophotometer.

DETAILED DESCRIPTION OF THE INVENTION

The adulteration detecting reagent used in process of the instant invention comprises an aqueous solution of a buffered carbonyl indicator, which is mixed with the urine or other fluid sample to be tested. The buffering of the carbonyl indicator acts to stabilize pH, which is critical to the carbonyl indicator reaction and to reagent storage. The adulteration detecting reagent also has a surfactant which aids in solubility (i.e., acts to decrease surface tension and increase carbonyl indicator solubility), hereinafter referred to as the adulteration reagent. The entire mixture is then inserted into the instrument, and the absorbance read for comparison against known standards.

The formulation for the adulteration reagent can be prepared in accordance with Examples I and II as follows:

EXAMPLE 1

Prepare a solution per liter containing:

0.01 g 2.4-dinitrophenylhydrazine (or other indicator as indicated in the list below, or mixture of indicators);

0.01 ml Brij 35 solution, 30% w/v (polyoxethylene 23 lauryl ether);

60.0 ml Hydrochloric Acid (HCl);

adjust the pH of the solution to 4.00 with sodium hydroxide or hydrochloric acid, as appropriate. The solution is then brought to total volume of 1.0 liter with reagent grade water.

EXAMPLE II

A preferred solution per liter is the following:

0.6 g 4-nitrophenylhydrazine;

10. ml of isopropanol or other lower alkyl alcohol;

0.01 ml polyethylene 23 lauryl ether;

60.0 ml HCl;

No pH adjustment is necessary for this solution.

OTHER INDICATORS

Indicators that can be substituted for the above mentioned hydrazines;

0.01 g Hydrazine;

0.01 g Phenylhydrazine;

0.01 g Semicarbazide Hydrochloride;

0.01 g Hydroxylamine Hydrochloride

NOTE: the reagent solution HCl content varies, with a change in indicators as follows:

| Indicator | Changes to formula |
|---|---|
| Hydrazine | no HCl added, temperature of instrument set at 37 degrees centigrade |
| Phenylhydrazine | HCl replaced with 1.0 N CH$_3$COOH |
| Semicarbizide Hydrochloride - no HCl added | |
| Hydroxylamine Hydrochloride - no HCl added | |

Formulation for the Low Calibrator is prepared with 3 g/l of vanillin and which is added to reagent grade distilled water.

The reagent system of the instant invention is intended for use on automatic analyzers, such as enzyme immunoassay analyzers (EMIT), such as Olymppus Au 5000 series, Hitachi 700 series, among others. On these instruments, the reagent is used in the following manner: 10 uL of urine sample is placed in a sample tube and mixed with 300 uL of adulteration reagent. The absorbance of the samples and calibrator is then measured a wavelength between 400 and 450 (ideally 405). The instrument spectrophotometer is set at 405 nm, and the calibrator value of the instrument is set at the low calibrator value; i.e., if the absorbance of the unknown sample is higher than the low calibrator then the sample has the adulterant normal by-product of human metabolism. If the unknown sample has an absorbance below the low calibrator, then the unknown sample is negative for the presence of the adulterant.

In the instant invention, when urine which has been adulterated, resulting in an increase in absorbance, is mixed with the reagent system in the prescribed ratio, the indicator will cause the sample mixture to increase in absorbance, depending on whether the adulterant is present or not. Such indication may be seen by manual inspection, but is especially intended for use in automatic analyzers, such as those which employ spectrophotometric means of inspection.

Specifications for running the urine sample through three specific instruments, of the clinical chemistry type Olympus, Hitachi, and Monarch, are listed below. The settings are intended as guidelines, and are set forth with the understanding that those skilled the art would recognize that such parameters will vary from instrument to instrument. The suggested specifications are as follows:

| Parameter Settings for Olympus AU5000 | |
|---|---|
| Measuring point: | S-0 |
| | E-3 |
| Reagent O.D.: | −2.00 to 2.00 |
| Normal High: | 10000 (* value obtained from positive control) |
| Normal Low: | −1000 (* value obtained from low calibrator) |
| QC Group No.: | 1    0 |
| | 2    0 |
| Sample vol: | 10 uL |
| Reagent vol: | 300 uL |
| Method: | END |
| Wavelength 1: | 405 NM |
| Wavelength 2: | 0 |
| Slope: | + |
| W 3 Operation: | R1 YES |
| | R2 NO |
| Calibration method: | m-cal |
| OD-CONC; | 0.000 |
| Point 1 OD.: | 0.00 |
| Factor: | 10,000 |
| Concentration: | 0 |
| Parameter Settings for Monarch | |
| Identification Parameters: | |
| Test code | 116 |
| Test name | aD |
| Test mnemonic | aD |
| Optical mode | Absorbance |
| Response algorithm | Final point |
| Result algorithm | Linear |
| Loading Parameters: | |
| Loading type | Load Analyze |
| Reagent blank | on |

-continued

| | |
|---|---|
| Reference type | Diluent |
| Calibrator type | Test specific |
| Sample volume | 5 uL |
| Sample diluent | 5 uL |
| Reagent diluent | 10 uL |
| 1st reagent | 220 uL |
| 2nd reagent | 0 uL |
| 1st rgt bar code | 1 k |
| Data Acquisition Parameters: | |
| Analysis type | Mix run |
| Temperature | 25 C. |
| Delay time | 30 sec |
| Interval time | 30 sec |
| No. of data points | 1 |
| Filter 1 | 405 nm |
| Filter 2 | 405 nm |
| Monochromator 1 | 405 nm |
| Monochromator 2 | 405 nm |
| Compatibility | None |
| Data Integrity Parameters: | |
| Integrity test | Normal range |
| Lower Limit | * determined by low calib. |
| Upper Limit | * determined by pos. control |
| Data Fit Parameters: | |
| Calibrator 1 | Low calibrator |
| Calibrator 2 | none |
| Correction mode | none |
| Units | none |
| No. of decimal places | 4 |
| Calculated Parameters: | |
| Data edited | (date) |
| Time edited | (time) |
| Run time | 30 sec |
| Parameter Settings for Hitachi 700 series | |
| Test: | [aD] |
| Assay code: | [1POINT]:[40]-[0] |
| Sample volume: | [10] [5] |
| R1 Volume: | [300] [5] [NO] |
| R2 Volume: | [ ] [ ] [NO] |
| Wavelength: | [ ] [405] |
| Calib. Method: | [Linear] [0] [0] |
| STD.(1)Conc.-POS: | [*] - [1] * Low Calib. value |
| STD.(2)Conc.-POS: | [ ] - [ ] |
| STD.(3)Conc.-POS: | [ ] - [ ] |
| STD.(4)Conc.-POS: | [ ] - [ ] |
| STD.(5)Conc.-POS: | [ ] - [ ] |
| STD.(6)Conc.-POS: | [ ] - [ ] |
| SD Limit: | [1.0] |
| Duplicate Limit: | [1000] |
| Sensitivity Limit: | [0] |
| ABS. Limit (INC/DEC): | [2000] [INCREASE] |
| Prozone Limit: | [0] [LOWER] |
| Expected Value: | [1.005]–[1.030] |
| Tech. Limit: | [1.003]–[1.035] |
| Instrument factor: | [1.0] |

It is recommended that calibrator value for the automated analyzers be set at the low calibrator value, with the instrument set to flag values at or above the low calibrator.

EXAMPLE III

Five hundred and seventy two (572) specimens were assayed for the presence of the urine adulterant (i.e., Urine Aid-gluteraldehyde) using the reagent system of the invention on the Olympus AU5000 by an independent laboratory.

The adulterant reagent of the instant invention used, per manufacturer's instruction in the OLYMPUS AU5000 assay.

The urine adulteration detecting reagent for the 572 urine samples measured by the OLYMPUS AU5000 method are as follows:

Total # of specimens run: 572
Total positive for urine adulterant: 10
% positive in random population: 1.75%
Mean low calibrator value: 2315 at 405 nm
Mean positive control value: 3241 at 405 nm After correlating the data, 1.75% of the random population was positive for the presence of the urine adulterant (or 10 out of 572 specimens), suggesting confirmation of the results by the reference method IR, NMR, or GC-MS.

It will be understood that the embodiments that a person skilled in the art may make variations and modifications without departing from the spirit and scope of the invention. All such modifications and variations are to be included within the scope of the invention as defined in the appended claims:

I claim:

1. A method for the detection of glutaraldehyde adulterant in a urine sample comprising (a) obtaining an aliquot of urine from an unknown sample and an aliquot of a standard low calibrator, inserting both the sample and low calibrator aliquot in an automatic chemical analyzer, (b) separately mixing both of the aliquots with an aqueous carbonyl indicator in a reagent mixture, comprising an indicator and surfactant wherein the indicator is selected from the group consisting of 2,4-dinitrophenylhydrazine, 4-nitrophenylhydrazine, hydrazine, phenylhydrazine, semicarbazide hydrochloride, and hydroxylamine hydrochloride, (c) performing spectrophotometric absorbance readings on the mixtures of (b) above, wherein the spectrophotometric absorbance readings from the mixtures of reagent with the sample and low calibrator indicate the presence of the adulterant if the absorbance of the sample mixture is greater than or equal to the absorbance of the low calibrator mixture.

2. The method according to claim 1 wherein the spectrophotometric wavelength employed is from 340 nm to 800 nm.

3. The method according to claim 1 wherein the carbonyl indicator mixed with the aliquot is 2,4-dinitrophenylhydrazine.

4. The method according to claim 1 wherein the carbonyl indicator mixed with the aliquot is 4-nitrophenylhydrazine.

5. A method for detection of glutaraldehyde adulterant in a urine sample comprising (a) obtaining an aliquot of urine from a sample and a standard low calibrator, inserting both of the aliquots in an automatic chemical analyzer, (b) separately mixing the aliquots with a reagent mixture containing, water, hydrochloric acid, a surfactant, a lower alkyl alcohol and 4-nitrophenylhydrazine, (c) performing spectrophotometric absorbance reading on the mixtures of (b) above at a preselected wavelength wherein the spectrophotometric absorbance reading from the aliquot of urine with reagent mixture indicates the presence of the adulterant, if the absorbance is greater than or equal to the absorbance of the mixture of low calibrator and reagent.

6. The method according to claim 5 wherein the reagent mixture of (b) contains 0.6 g 4-nitrophenylhydrazine, 10.0 ml of isopropanol, 0.1 ml polyethylene 23 lauryl ether 60.0 ml HCl and the remainder distilled water to make 7. The method according to claim 1 wherein the mixture of (b) contains a polyoxethylene 23 lauryl ether surfactant and the pH is adjusted to about 4.

8. The method according to claim 5 wherein the wavelength employed is between 400 and 450 nm.

* * * * *